(12) United States Patent
Tu (10) Patent No.: US 10,843,365 B2
(45) Date of Patent: Nov. 24, 2020

(54) SHAPE CUTTING DEVICE FOR SKIN ELECTRODE PATCH

(71) Applicant: Feng Ching Tu, Taipei (TW)

(72) Inventor: Feng Ching Tu, Taipei (TW)

( * ) Notice: Subject to any disclaimer, the term of this patent is extended or adjusted under 35 U.S.C. 154(b) by 347 days.

(21) Appl. No.: 15/357,088

(22) Filed: Nov. 21, 2016

(65) Prior Publication Data

US 2018/0141231 A1     May 24, 2018

(51) Int. Cl.
| | | |
|---|---|---|
| *B26F 1/38* | (2006.01) | |
| *B26D 7/20* | (2006.01) | |
| *A61N 1/04* | (2006.01) | |
| *B26D 7/06* | (2006.01) | |

(52) U.S. Cl.
CPC ............ *B26F 1/384* (2013.01); *A61N 1/0492* (2013.01); *B26D 7/0625* (2013.01); *B26D 7/204* (2013.01)

(58) Field of Classification Search
CPC ....... B26F 1/384; B26D 7/0625; B26D 7/204; A61N 1/0492
See application file for complete search history.

(56) References Cited

U.S. PATENT DOCUMENTS

| | | | | | |
|---|---|---|---|---|---|
| 3,383,969 | A | * | 5/1968 | Saunders | B26F 1/44 83/663 |
| 4,085,639 | A | * | 4/1978 | Marconi | B21D 45/00 83/157 |
| 4,248,117 | A | * | 2/1981 | Bugnone | B23P 15/406 83/863 |
| 4,635,642 | A | * | 1/1987 | Cartmell | A61B 5/04087 600/392 |
| 4,795,516 | A | * | 1/1989 | Strand | A61B 5/04087 156/235 |
| 4,798,642 | A | * | 1/1989 | Craighead | A61B 5/04087 156/252 |
| 5,405,486 | A | * | 4/1995 | Sablotsky | A61F 13/0276 156/250 |
| 5,713,128 | A | * | 2/1998 | Schrenk | A61B 18/16 156/226 |
| 5,967,009 | A | * | 10/1999 | Truttmann | B26F 1/44 83/346 |
| 2003/0134545 | A1 | * | 7/2003 | McAdams | A61N 1/0492 600/372 |
| 2004/0261939 | A1 | * | 12/2004 | Ogle | A61F 13/15723 156/269 |

(Continued)

*Primary Examiner* — Peter Dungba Vo
*Assistant Examiner* — Jeffrey T Carley
(74) *Attorney, Agent, or Firm* — Muncy, Geissler, Olds & Lowe, P.C.

(57) ABSTRACT

A shape cutting device of a skin electrode patch includes: a substrate conveyor for transmitting a coated substrate portion and a conductive adhesive portion; a positioning conveyor; a fitted shape cutting module installed in a successive portion of the positioning conveyor and having two pressing wheels and a shape cutting unit, and the two pressing wheels being provided for pressing the coated substrate portion and the conductive adhesive portion, and the shape cutting unit including a roller body with at least one cutting knife which is in a geometrical shape and includes two side cutters and a first-end cutter at an axial end, and opposite ends of the first-end cutter having two second-end cutters, and a gap being formed in the two second-end cutters. The cutting knife has a design that integrates the transmission feature and the efficiency of the whole production line.

3 Claims, 7 Drawing Sheets

(56) References Cited

U.S. PATENT DOCUMENTS

| | | | |
|---|---|---|---|
| 2007/0039443 A1* | 2/2007 | Takahashi | B26D 7/265 83/659 |
| 2011/0056621 A1* | 3/2011 | Quinn | A61F 13/0283 156/269 |
| 2012/0077661 A1* | 3/2012 | Oonishi | A61F 13/15723 493/471 |
| 2015/0044338 A1* | 2/2015 | Nagle | A23G 3/0025 426/302 |
| 2015/0313499 A1 | 11/2015 | Sohn | |

* cited by examiner

SHAPE CUTTING DEVICE FOR SKIN ELECTRODE PATCH

FIELD OF THE INVENTION

The present invention relates to a shape cutting device of a skin electrode patch, and more particularly to the device used for shape cutting or material cutting in the manufacture of skin electrode patches, and the device provides a continuous cutting effect and a strong structural strength to prevent breakdowns in production lines.

BACKGROUND OF THE INVENTION

1. Description of the Related Art

Present electrode skin treatment devices used for treating or soothing various types of nervous and muscular pains and have the effects of improving neuromuscular excitability, adjusting meridian functions and enhancing blood circulation. The electrode treatment devices are usually used together with a skin electrode patch, and the skin electrode patch is attached to a position of a human body to be treated or soothed, the skin electrode patch conceals a power supply device and circuits capable of generating a pulse output of positive and negative electrodes therein, so that the external appearance shows a structure of a seamless waterproof object, and the skin electrode patch is a self-adhesive patch capable of generating electrode pulses.

Figure 1:
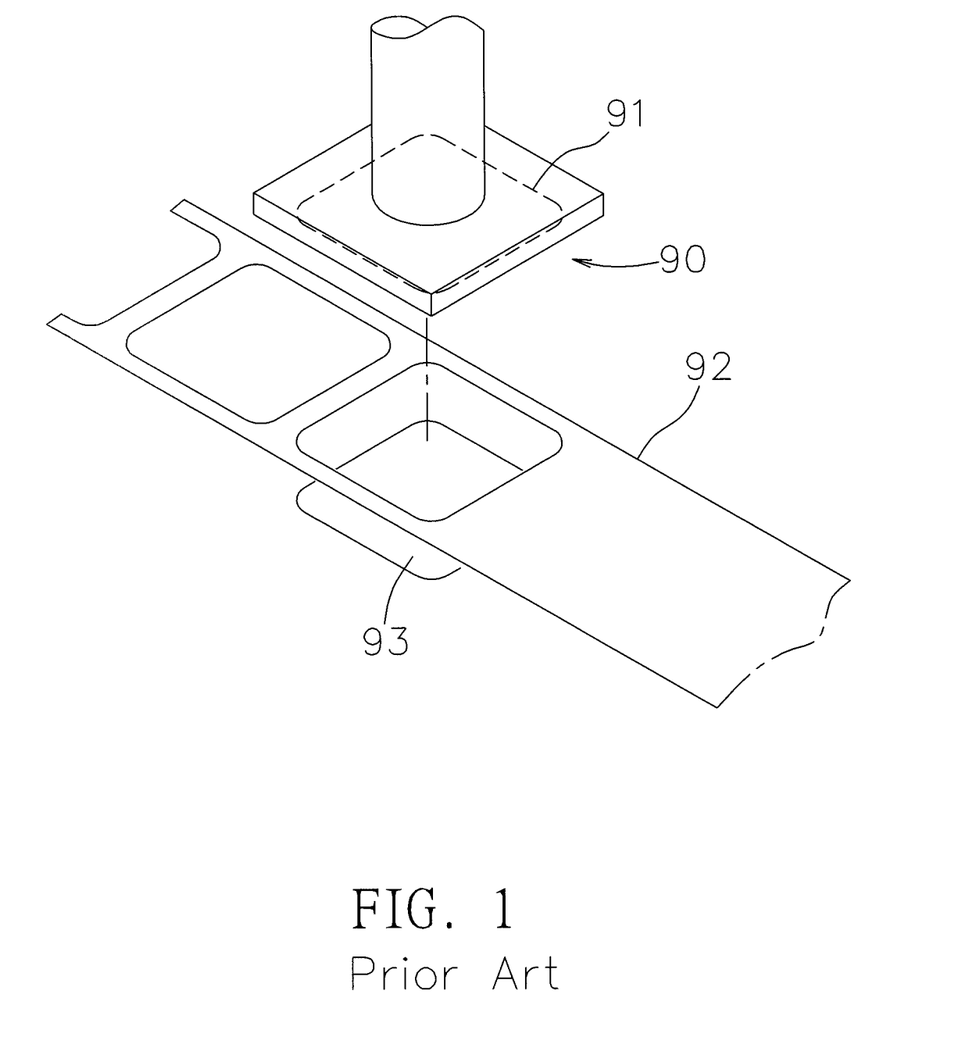
FIG. 1 is a schematic view of a shape cutting assembly of a conventional electrode patch.
Figure 1A:
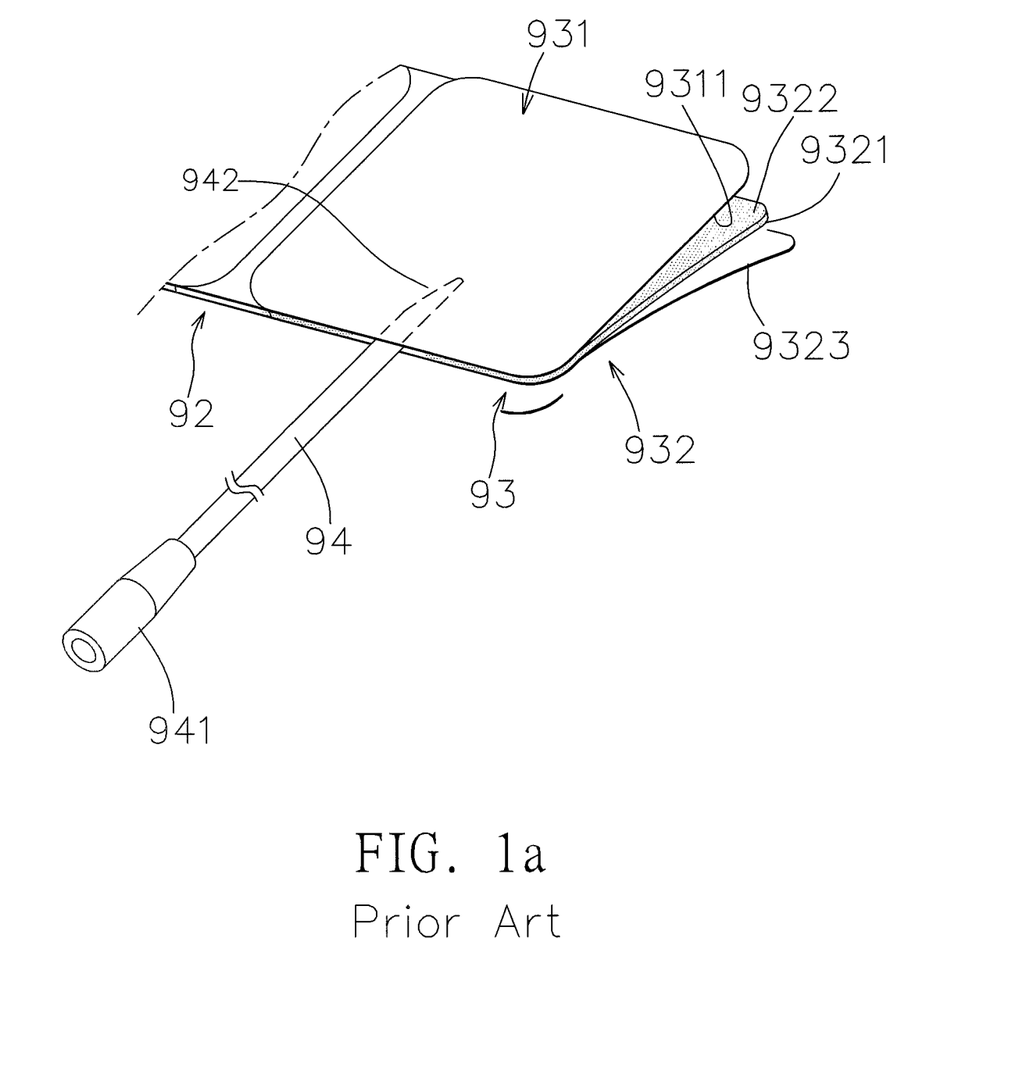
FIG. 1a is a schematic view of an electrode lead of a conventional electrode patch.

With reference to FIGS. 1 and 1a for the assembly and manufacture of a conventional electrode patch, a shape cutting device 90 is provided for cutting a patch material strip 92 into a specific shape, and the shape cutting device 90 has a cutting knife 91, and the cutting knife 91 cuts the patch material strip 92 equidistantly into plural pieces of electrode patches 93, wherein the electrode patch 93 needs to manufacture an electrode lead 94 separately, and an end of the electrode lead 94 is a power connector 941, and the power connector 941 acts as an input channel of an external power supply, and the other end of the electrode lead 94 opposite to the power connector 941 is an exposed conductive terminal 942, and the power connector 941 and the exposed conductive terminal are electrically conducted with one another.

Wherein, the electrode patch 93 includes a coated substrate layer 931 and a conductive adhesive layer 932, and a glue layer 9311 is adhered to a side of the coated substrate layer 931. The conductive adhesive layer 932 includes an adhesive layer body 9321, and a conductive layer 9322 is adhered to a side of the adhesive layer body 9321, and a release layer 9323 (such as a release paper) is attached onto the other side of the adhesive layer body 9321. During assembling, the glue layer 9311 of the coated substrate layer 931 is adhered with the exposed conductive terminal 942 of the electrode lead 94, and then the coated substrate layer 9311 and the conductive adhesive layer 932 are laminated and adhered with one another, so that the electrode lead 94 is fixed between the coated substrate layer 931 and the conductive adhesive layer 932, and the electrode lead 94 and the conductive layer 9322 are electrically conducted with one another. Now, the power connector 941 of the electrode lead 94 is protruded to the outside as shown in the figure, and then the skin electrode patch 93 is cut into a specific shape.

In the assembling and manufacturing method of the aforementioned skin electrode patch 93, each step is performed manually, and the skin electrode patch 93 must be cut into a specific shape first, and then the electrode lead 94 is installed to the coated substrate layer 931 or the conductive adhesive layer 932 manually before the lamination process takes place. Obviously, the conventional method is unfavorable to enhancing the assembling speed of the production line and requires further improvements. Therefore, it is an important subject for related manufacturers and designer to develop and design a novel electrode patch to overcome the drawbacks of the conventional electrode patch.

In view of the drawbacks of the conventional electrode patch and its manufacturing method, the inventor of the present invention based on years of experience in the related industry to conduct researches and experiments and finally developed a shape cutting device of a skin electrode patch in accordance with the present invention with manufacturing convenience and efficiency.

2. Summary of the Invention

Therefore, it is a primary objective of the present invention to provide a shape cutting device of a skin electrode patch that allows the electrode lead to be assembled and installed conveniently in a production line during the electrode patch manufacturing process.

Another objective of the present invention is to provide a roller type configuration of the cutting knife to facilitate improving the shape cutting efficiency.

To achieve the aforementioned and other objectives, the present invention discloses a shape cutting device of a skin electrode patch, comprising: a substrate conveyor, for transmitting a strip coated substrate portion and a conductive adhesive portion; a positioning conveyor, including a conveyor belt; a fitted shape cutting module, installed in a successive portion of the positioning conveyor, and having two pressing wheels and a shape cutting unit, and the two pressing wheels pressing the coated substrate portion and the conductive adhesive portion, and the shape cutting unit including a roller body, and the roller body having at least one cutting knife installed thereon, and the cutting knife being in a geometrical shape and including the cutting knife having two protruding side cutters and a first-end cutter of an axial end, and opposite ends of the first-end cutter having two second-end cutters, and the first-end cutter being coupled to the side cutters on both sides, and the two side cutters and the two second-end cutters being coupled to one another, and a shape cutting area inside the cutting knife being formed and enclosed by the first-end cutter, the two side cutters and the two second-end cutters, and a gap being formed between the two second-end cutters; wherein, the cutting knife is used for cutting the coated substrate portion, an attached body of the conductive adhesive portion into a shape.

In the shape cutting device, the conveyor belt has a plurality of positioning tools for positioning an electrode lead.

In the shape cutting device, the roller body is installed to a transmission shaft.

In the shape cutting device, the cutting knife includes two protruding side cutters and a first-end cutter at an axial end, and opposite ends of the first-end cutter have two second-end cutters, and the first-end cutter and the side cutter on both sides are coupled to one another, and the two side cutters and the two second-end cutters are coupled to one another, such that a shape cutting area inside the cutting knife is formed and enclosed by the first-end cutter, the two side cutters and the two second-end cutters, and a gap is formed between the two second-end cutters.

The present invention further provides a shape cutting unit of a skin electrode patch, and the shape cutting unit further comprises a transmission shaft and a roller body, and the roller body has at least one cutting knife and the cutting knife is substantially in a geometrical shape, and the cutting knife includes two protruding side cutters and first-end cutter of an axial end, and opposite ends of the first-end cutter have two second-end cutters respectively, and the first-end cutter is coupled to the side cutters on both sides, and the two side cutters are coupled to the two second-end cutters, and a shape cutting area inside the cutting knife is formed and enclosed by the first-end cutter, the two side cutters and the two second-end cutters, and a gap is formed between the two second-end cutters.

In the shape cutting unit, the cutting knife is substantially in an arc shape, and the first-end cutter, the side cutter, and the second-end cutter of the cutting knife form an end and two side edges of the arc shaped cutting knife, and the gap forms the other end gap of the arc shaped cutting knife.

DESCRIPTION OF THE PREFERRED EMBODIMENTS

The above and other objects, features and advantages of this disclosure will become apparent from the following detailed description taken with the accompanying drawings. It is noteworthy that the drawings are intended for illustrating the present invention only, but not for limiting the scope of the invention, and the drawings are not necessarily drawn according to the actual shape, size or proportion of the device.

Figure 2:
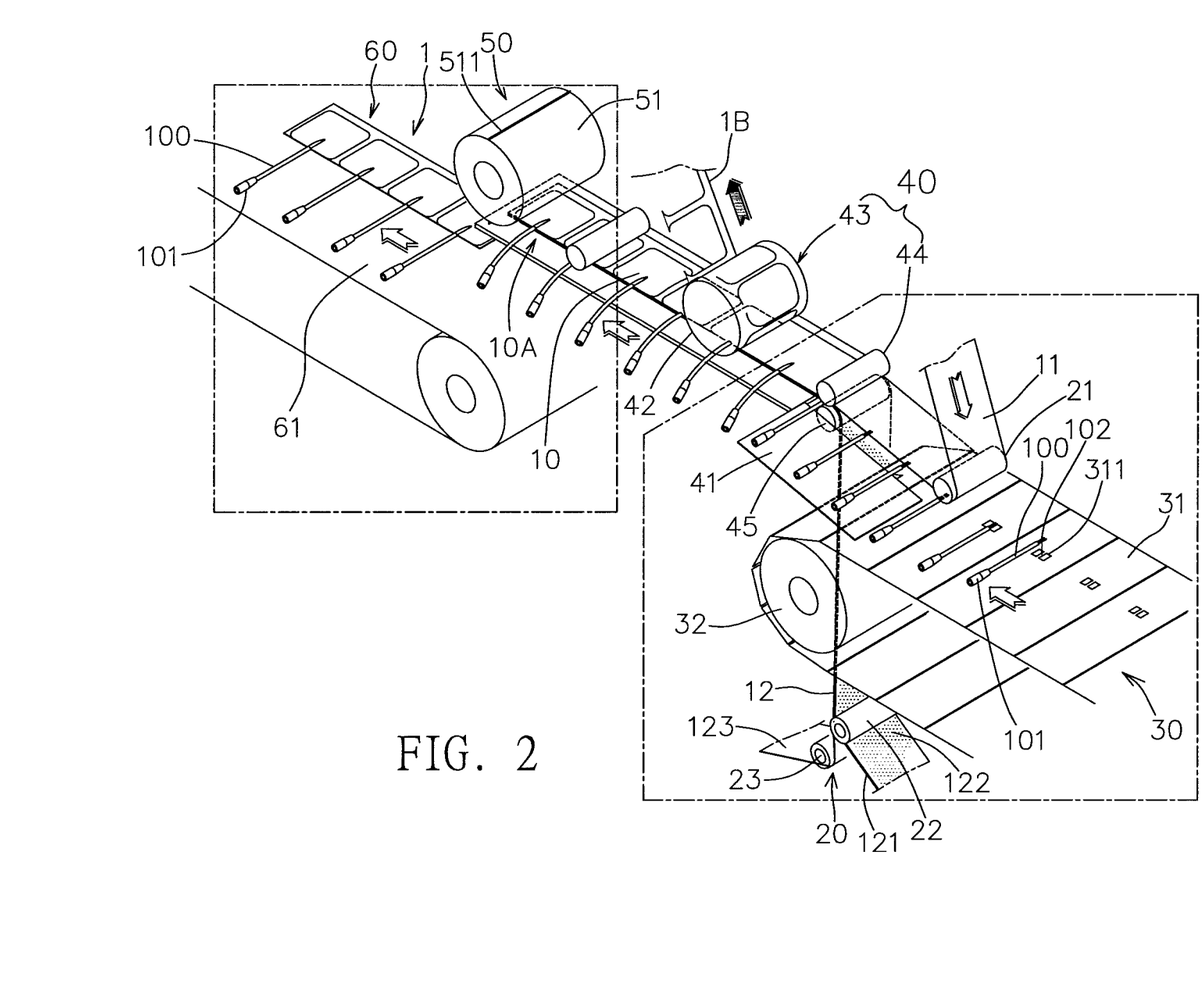
FIG. 2 is a flow chart showing the operation of the present invention.

With reference to FIG. 2 for an electrode patch module 1 produced in a production line by using a shape cutting device of a skin electrode patch of the present invention, the electrode patch module 1 comprises a plurality of electrode patches 10, and production of the present invention the production line comprises a substrate conveyor 20, a positioning conveyor 30, a fitted shape cutting module 40, a section cutting device 50 and a finish products conveying device 60, wherein the substrate conveyor 20 includes a first transmission roller 21 on a side and a second transmission roller 22 and a third transmission roller 23 on the other side. In this embodiment, the first transmission roller 21 is for transmitting a strip coated substrate portion 11 and then transmitting to the positioning conveyor 30; and the second transmission roller 22 and the third transmission roller 23 are provided for transmitting the strip conductive adhesive portion 12 and the release layer 123 respectively, and the conductive adhesive portion 12 is comprised of a glue layer 121 and a conductive layer 122 on the glue layer 121, and the conductive adhesive portion 12 and the release layer 123 are attached during the transmission, and then the conductive adhesive portion 12 with the attached release layer 123 is transmitted to a pressing wheel 45 of a fitted shape cutting module 40. In addition, the coated substrate portion 11 and the conductive adhesive portion 12 are not limited to the aforementioned assembly only.

The positioning conveyor 30 includes a conveyor belt 31 and a transmission wheel 32 disposed at both ends of the conveyor belt 31 respectively. In this embodiment, the conveyor belt is operable in a loop, and the transmission wheel 32 is provided for supplying the power for moving the conveyor belt 31 in a loop, and the conveyor belt 31 has a plurality of positioning tools 311 installed thereon, and the positioning tool 311 is for positioning an electrode lead 100, and both ends of the electrode lead 100 have a conductive wire connector 101 and an electrode terminal 102. During the assembling and use of the positioning conveyor 30, the positioning tool 311 is provided for positioning the electrode lead 100. In this embodiment, the electrode terminal 102 is embedded and positioned by the positioning tool 311, so that the electrode lead 100 is positioned onto the conveyor belt 31 and moved and conveyed accordingly.

The fitted shape cutting module 40 is installed in the successive portion of the positioning conveyor 30 and includes a stripping guide plate 41, a pressing wheel 44, 45, a carrying plate 42 and a shape cutting unit 43, and the stripping guide plate 41 is slantingly coupled to an end portion of the positioning conveyor 30, and the front end of the stripping guide plate 41 is configured to be corresponsive to the first transmission roller 21 for transmitting the coated substrate portion 11. In the meantime, the first transmission roller 21 is also disposed in the rear upper portion of the conveyor belt 31, and the pressing wheels 44, 45 are installed in the successive portion of the stripping guide plate 41, and the conductive adhesive portion 12 is transmitted through the pressing wheel 45 to the fitted shape cutting module 40, and the pressing wheels 44, 45 are provided for pressing the conductive adhesive portion 12 and the coated substrate portion 11 into a strip, and the carrying plate 42 is installed in the successive portion of the pressing wheels 44, 45, and the shape cutting unit 43 is installed above an appropriate position of the carrying plate 42.

Figure 3:
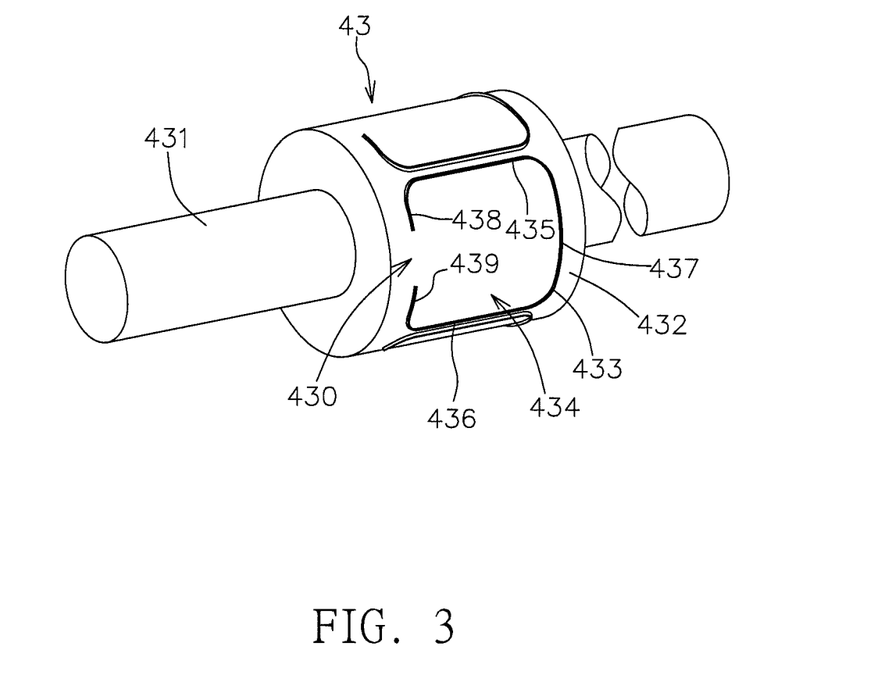
FIG. 3 is a perspective view of a shape cutting unit of the present invention.
Figure 4:
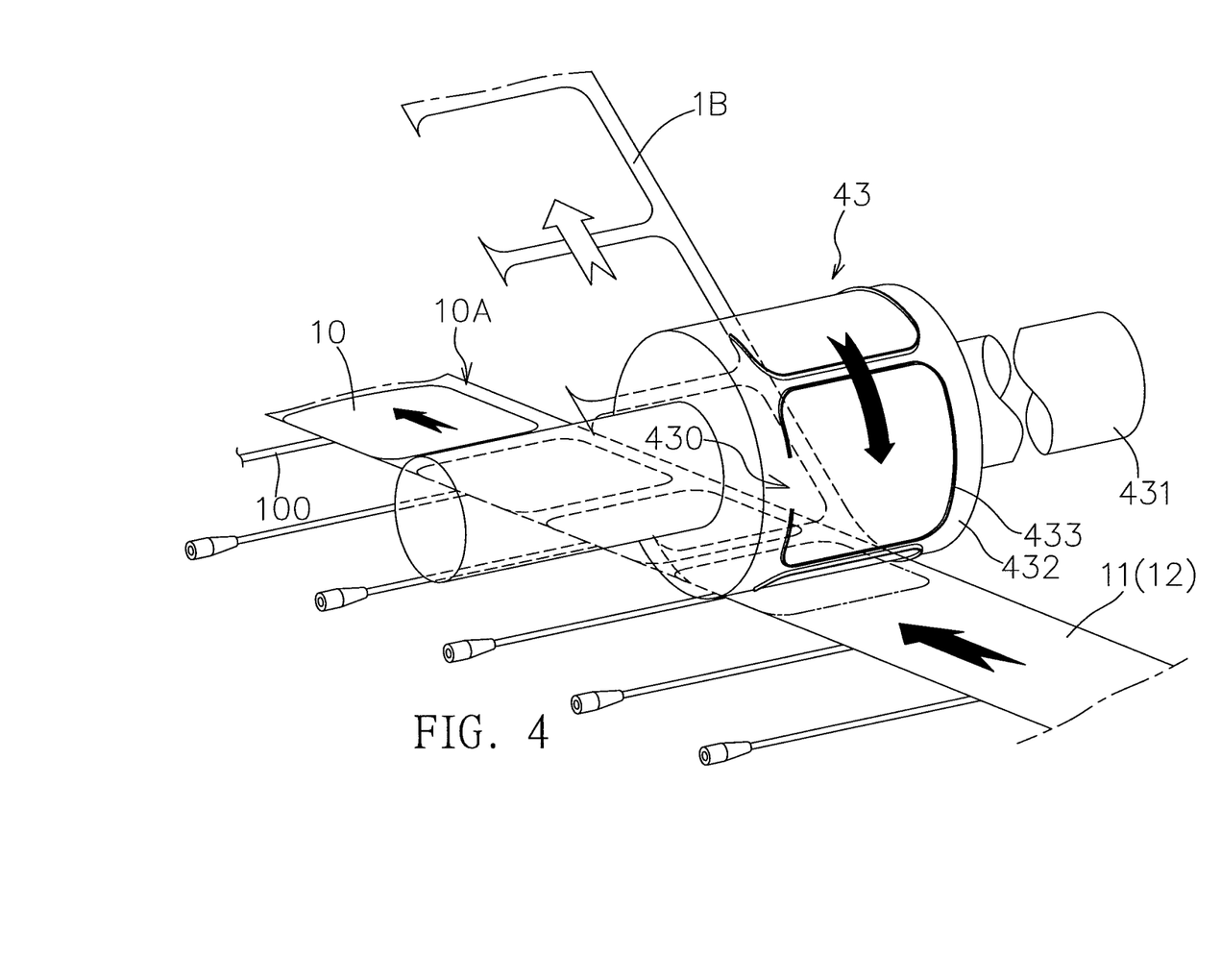
FIG. 4 is a perspective view showing a shape cutting operation of a shape cutting unit of the present invention.

In FIGS. 3 and 4, the shape cutting unit 43 comprises a transmission shaft 431 and a roller body 432, and the roller body 432 has a plurality of cutting knives 433, and the cutting knives 433 are substantially in a geometrical shape and includes two protruding side cutters 435, 436 and a first-end cutter 437 at an axial end, and opposite ends of the first-end cutter 437 have a second-end cutter 438, 439, wherein the first-end cutter 437 is coupled to the side cutters 435, 436 on both sides (connected at an arc end corner), and the side cutter 435 and the second-end cutter 438, and the side cutter 436 and the second-end cutter 439 are coupled respectively (connected at an arc end corner) to enclose and form a shape cutting area 434 inside the cutting knife 433, and a gap 430 is formed between the second-end cutter 438, 439, and the gap 430 does not have the installation of the cutting knife 433.

Figure 3A:
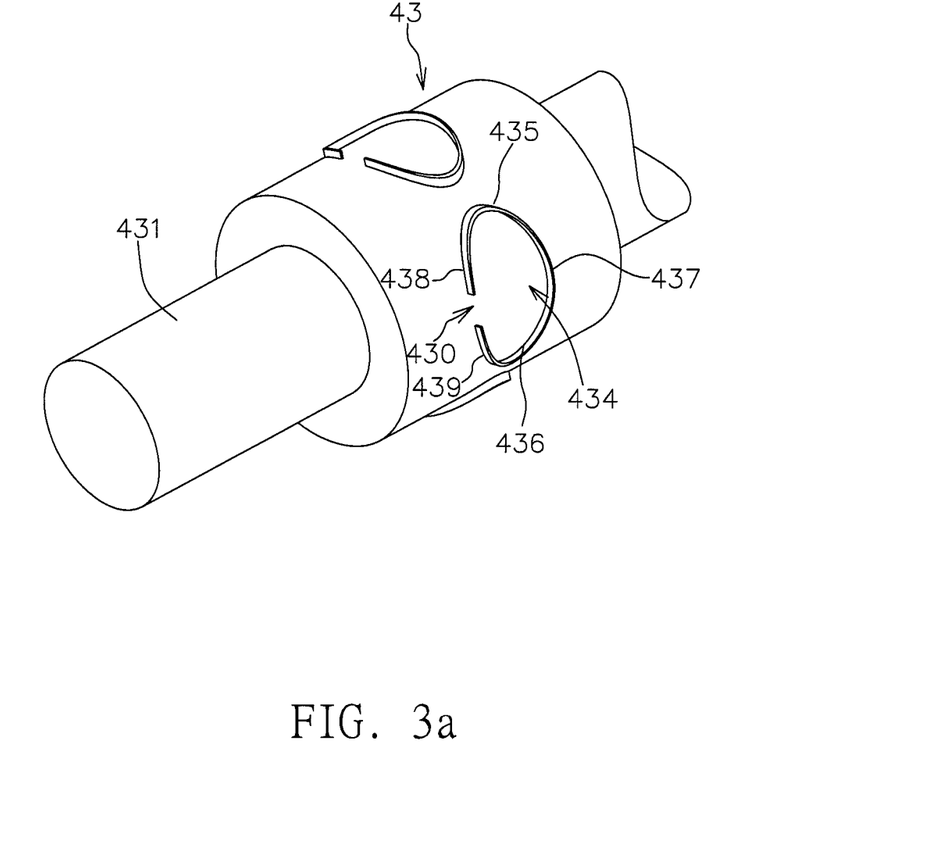
FIG. 3a is a perspective view of a shape cutting unit of another embodiment of the present invention.

The cutting knife 433 is a substantially square or rectangular assembly. In other embodiment, the cutting knife 433 is a geometrical shaped assembly (as shown in FIG. 3a), and the arc geometrical shape includes but not limited to a circular, elliptical or egg shape, and the geometrical shaped cutting knife 433 also has a gap, and the gap may be the gap 430. In other words, the central portion of the first-end cutter 437 of the cutting knife 433 forms an end of the arc shaped cutting knife 433, and t both sides of the side cutters 435, 436, the second-end cutters 438, 439 and the first-end cutter 437 form two side edges of the arc shaped cutting knife 433, and the gap 430 forms the other end gap of the arc shaped cutting knife 433, and the gap 430 does not have the installation of the cutting knife 433.

The section cutting device 50 is installed at the rear portion of the fitted shape cutting module 40, and the section cutting device 50 includes a section cutting wheel 51. The finish products conveying device 60 is installed at the successive portion of the section cutting device 50, and the finish products conveying device 60 includes a conveying portion 61.

In an application of shape cutting device of a skin electrode patch of the present invention, the coated substrate portion 11 is pulled backward by a pulling force, and the coated substrate portion 11 finally enters into the rear upper portion of the conveyor belt 31 from the first transmission roller 21, so that the electrode lead 100 pre-installed on the conveyor belt 31 is attached onto a glue layer of the coated substrate portion 11 (not shown in the figure), and then moved together with the coated substrate portion 11. In this embodiment, the electrode terminal 102 of the electrode lead 100 is adhered to the coated substrate portion 11 (or the glue layer) and then the coated substrate portion 11 is entered into the stripping guide plate 41 and continuously moved further. When the coated substrate portion 11 is moved to the pressing wheels 44, 45, it is attached to the conductive adhesive portion 12 having the release layer 123 attached below. The conductive adhesive portion 12 is also pulled backward by a pulling force, and the conductive adhesive portion 12 is finally entered from the pressing wheel 45 into the carrying plate 42. Since the coated substrate portion 11 and the conductive adhesive portion 12 are entered into the carrying plate 42 of the fitted shape cutting module 40 through the pressing wheel 44, 45, so that the coated substrate portion 11 and the conductive adhesive portion 12 are laminated and adhered with each other by the pressing wheels 44, 45. Now, the electrode lead 100 (or electrode terminal 102) is clamped and positioned between the coated substrate portion 11 and the conductive adhesive portion 12, and the conductive wire connector 101 is protruded out from the outside of the coated substrate portion 11 and the conductive adhesive portion 12. In this embodiment, the electrode terminal 102 of the conductive wire connector 101 is clamped and positioned between the coated substrate portion 11 and the conductive adhesive portion 12, and the remaining ones are protruded out from the outer side of the coated substrate portion 11 and the conductive adhesive portion 12.

Figure 5:
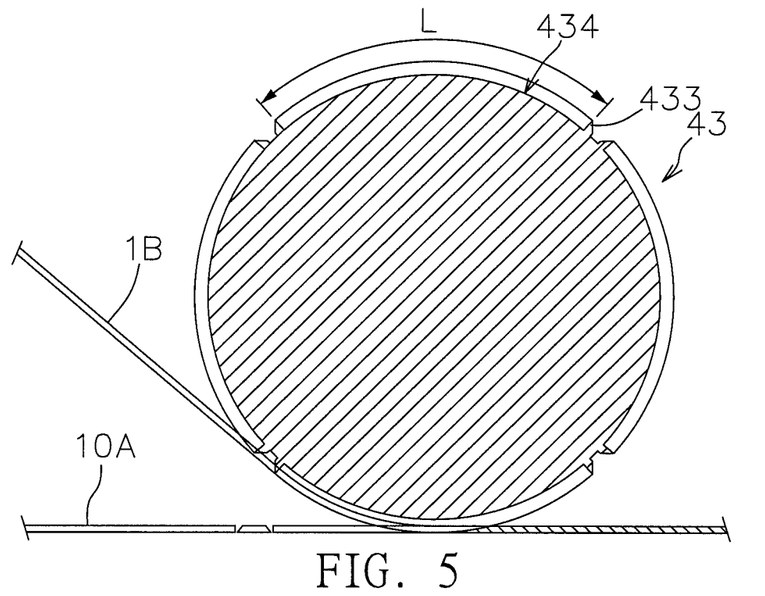
FIG. 5 is a cross-sectional view showing a shape cutting operation of a shape cutting unit of the present invention.
Figure 6:
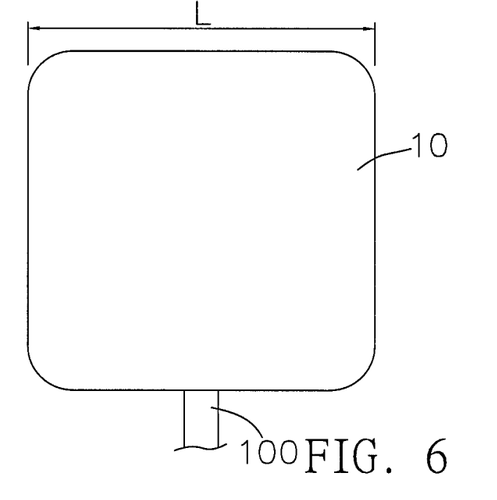
FIG. 6 is a schematic view of an electrode patch of the present invention after the shape cutting.

With reference to FIGS. 5 and 6, the electrode lead 100 is clamped and secured between the attached coated substrate portion 11 and conductive adhesive portion 12 and continuously moved at the carrying plate 42. When the electrode lead 100 passes through the shape cutting unit 43, the attached body of the coated substrate portion 11 and the conductive adhesive portion 12 (together with the release layer 123) is cut into a specific shape by the cutting knife 433. In this embodiment, the cutting knife 433 has a wheel width L (which is the length between the two side cutters 435, 436), and the cut electrode patch 10 has a width equal to L, and the second-end cutters 438, 439 are substantially disposed at edges of the attached body, and the gap 430 is provided for preventing the electrode lead 100 from being cut or broken unintentionally, and the remaining material strip 1B of the attached body after the cutting is separated. After the shape cutting, the strip electrode patch module 10A is transmitted through the section cutting device 50 and cut by the section cutting wheel 51, such that the attached body of the strip coated substrate portion 11 and conductive adhesive portion 12 becomes a strip attached body, so as to form the electrode patch module 1. The electrode patch module 1 falls on the conveying portion 61 of the finish products conveying device 60, and the finish product is collected.

With the aforementioned assembly of the shape cutting device of a skin electrode patch of the present invention, the shape cutting device facilitates the electrode lead to be installed conveniently in the production during an electrode patch manufacturing process and has excellent manufacturing efficiency and stable quality. In the meantime, the cutting knife of present invention may be a roller type to provide a design with excellent structural assembly to facilitate the transmission in the whole production line and provide excellent efficiency for the shape cutting.

What is claimed is:

1. A shape cutting unit of a skin electrode patch, comprising a transmission shaft and a roller body, and the roller body having at least one cutting knife and the cutting knife being in a geometrical shape, and the cutting knife including two protruding side cutters and a first-end cutter, located adjacent to an end of the roller body, and the first-end cutter having at least two opposing ends, with two of the opposite ends of the first-end cutter each having one second-end cutter respectively, and the first-end cutter being coupled to the side cutters at two of the opposite ends, and the two side cutters being coupled to the two second-end cutters, and a shape cutting area inside the cutting knife being formed and enclosed by the first-end cutter, the two side cutters and the two second-end cutters, and only one gap being formed between the two second-end cutters of the cutting knife, the one gap being where the two second-end cutters of the cutting knife do not connect to each other, wherein the cutting knife is continuously unbroken from one of the two second-end cutters to another of the two second-cutters, and the one gap being provided for preventing a electrode lead from being cut.

2. The shape cutting unit of a skin electrode patch according to claim 1, wherein the cutting knife is an incomplete square or rectangle, having rounded corners and the one gap.

3. The shape cutting unit of a skin electrode patch according to claim 1, wherein the cutting knife is an incomplete circular, elliptical or egg shape with the one gap.

* * * * *